(12) United States Patent
Korpela et al.

(10) Patent No.: US 7,544,773 B2
(45) Date of Patent: Jun. 9, 2009

(54) ANTIMICROBIALS AGAINST PATHOGENIC BACTERIA AND METHOD FOR SCREENING THEM

(76) Inventors: Timo Kalevi Korpela, Kraatarinkatu 1 D 42, Turku (FI) FIN-20610; Anton Zavialov, Profsouznya str. 98-4-58, Moscow (RU) 117485; Vladimir Zav'yalov, Ul. Zavodskaya 10 fl 12, Lyubuchany (FI) 142380

( * ) Notice: Subject to any disclaimer, the term of this patent is extended or adjusted under 35 U.S.C. 154(b) by 700 days.

(21) Appl. No.: 10/619,256

(22) Filed: Jul. 14, 2003

(65) Prior Publication Data

US 2006/0106198 A1 May 18, 2006

(51) Int. Cl.
*A61K 38/04* (2006.01)
*A61K 38/00* (2006.01)
*C07K 5/00* (2006.01)
*C07K 7/00* (2006.01)
*C07K 16/00* (2006.01)
*C07K 17/00* (2006.01)

(52) U.S. Cl. .......................................... 530/329; 514/2
(58) Field of Classification Search ........................ None
See application file for complete search history.

(56) References Cited

U.S. PATENT DOCUMENTS 5,843,450 A * 12/1998 Dawson et al. ............ 424/189.1
6,001,823 A * 12/1999 Hultgren et al. ............... 514/99

FOREIGN PATENT DOCUMENTS

| WO | WO95/14028 | | 5/1995 |
| WO | WO 0032785 | * | 6/2000 |
| WO | WO01/10386 | | 2/2001 |
| WO | WO 02077183 | * | 10/2002 |

OTHER PUBLICATIONS

Hochheimer A. et al. "The Tungsten FormylMethanofuran Dehydrogenase From Methanobacterium thermoautotrophicum Contains Sequence Motifs Characteristic for Enzymes Containing Molybdenum Dinucleotide" 1995, Eur. J. Biochem. vol. 234, pp. 910-920.*
Zavyalov V.P et al. Specific high affinity binding of human interleukin . . . FEBS Letters 371 (1995) 65-68.
Flemmer K et al. Peptides inhibit complexation of the bacterial . . . Bioorganic & Medicinal Chemistry Letters 1995, vol. 5:9 927-932.
Zavialov A V. 2001 Secretion of recombinant proteins via . . . Applied and Environmental Microbiology 2001, p. 1805-1814.
Zavialov AV et al. 2003 Structure and Biogenesis of the Capsular F1 . . . Cell 113: 587-596.
Zavialov AV et al 2002 Donor strand complementation mechanim . . . Molecular Microbiology 45(1) 983-.
Zavialov et al. (2001) Secretion of recombinant proteins via Chperone/usher . . . Appl: and Env. Microbiology 67(4) 1805-1814.
Zavyalov et al. (1995) Specific high affinity binding of human interleukin . . . FEBS LEtt. 371: 65-68.
Zavyalov et al. (2003) Stucture and Biogenesis of the Capsular F1 Antigen from *Yersinia pestis* . . . Cell 113, pp. 587-596.
Flemmer K et al.(1995) Peptides inhibit complexation of the bacterial . . . Biorganic & MEdical Chemistry Letters.vol. 5 (9) pp. 927-932.

* cited by examiner

*Primary Examiner*—Andrew D. Kosar
*Assistant Examiner*—Maury Audet
(74) *Attorney, Agent, or Firm*—Dodds and Associates; John Dodds; Susanne Somersalo

(57) ABSTRACT

The present invention provides antimicrobials for efficient therapy of infections caused by bacterial pathogens. The antimicrobials include peptides corresponding to the active site of N-terminal extension of subunits composing specific adhesive organelles of virulence of pathogenic bacteria. These antimicrobial peptides inhibit surface expression of adhesive organelles and thus prevent development of infections caused by pathogenic bacteria. The invention describes also effective methods for screening molecules inhibiting the generation of the adhesive organelles.

5 Claims, 12 Drawing Sheets

A

```
            1         10        20
Caf1    ADLTASTTATATLVEPARITLT...
ΔCaf1   ADLTASTTS-----EPARITLT...
```

B

C

| Deleted variant of Caf1 | Position of deletion in the N-terminal extention | Polymerization of Caf1 in periplasm |
|---|---|---|
| d1 | $^1$AD****TTA$^9$ | +++ |
| d2 | $^1$AD*******TAT$^{12}$ | +++ |
| d3 | $^1$ADLTASTTS*****EPAR$^{18}$ | - |
| d4 | $^1$ADLTASTTS********R$^{18}$ | - |
| d5 | $^1$ADLTASTTATATLVEP****LTYK$^{24}$ | + |
| d6 | $^1$ADLTASTTATATLVEPARI****K$^{24}$ | +/- |

Adding
inhibitor

Protein
synthesis

1) Without an inhibitor: → —⋖⋖⋖⋖⋖  Virulence

2) With an inhibitor:  No virulence

Fig 9.

| Subunit | Organelle | N-terminal sequence |
|---|---|---|
| Caf1 | F1 capsular antigen | A D L T A S T T A T V |
| MyfA | Myf fibrillae | E P T V I N L E R P P V A K T T K T K |
| PsaA | PH6 antigen | S T V I N A T A S K D V S I S E V T R |
| AggA | AAF-I | A L A V A K T T N A C A T E T T |
| AafA | AAF-III | N F T S G T H A T T A C T K V D T N |
| AfaE-1 | AFA-I | A V D K H S G T T A C T T K T T |
| AfaE-2 | AFA-II | G F T P S G S N T T A C T T K T T |
| AfaE-3 | AFA-III | G F T P S G S N T T A C T T K T T |
| DraE | Dr haemagglutinin | A F T A S G N T A C T T K L T |
| AfaE-5 | AFA-V | A F T P S G T T A C T T K L T |
| DrbE-122 | Drb122 | T F Q P A S T T A C T T K L T |
| DrvE-121 | Drb121 | T F Q P A S T T A C G V E T V |
| DaaE | F1845 fimbriae | A T V V G D A T V Q G I T T S T |
| CseA | CS22 fimbriae | A A A G P T L T K E L A T T T |
| CS-3 | CS-3 fimbriae | G G A D G I R L G T A T A P V T |
| NfaE-111 | NFA | D G A G D G K N L G T A L N T |
| Dra2E | Dr-II | V N A G D G K N L G T A S G T T |
| NfaA | NFA-I | N D N V L N G V G A G N V K A V V A T A T |
| SefA | SEF-14 fimbriae | D A N G L N T V A G F V G N K A V V A V T A |
|  |  | D A N G L N T A G F V G N K A V V Q A T A |

Caf1M Gi donor sequence: 138ICNNLAFQVFVGVD125

Fig. 11.

ANTIMICROBIALS AGAINST PATHOGENIC BACTERIA AND METHOD FOR SCREENING THEM

This application contains sequence data provided on a computer readable diskette and as a paper version. The paper version of the sequence data is identical to the data provided on the diskette.

FIELD OF INVENTION

This invention is related to human and animal medicine and more specifically to improving the therapy/prophylaxis of infections caused by bacterial pathogens. This invention provides new antimicrobials for efficient therapy of the said infections to decrease therapeutic dose and to avoid side effects of harmful antimicrobials. The invention is also related to screening methods of putative antimicrobials.

BACKGROUND OF INVENTION

One of the most important steps in pathogenesis of infections is the attachment of microbes to host tissues. Pathogenic bacteria bind to target cells via specific adhesive organelles. Over 30 different operons, encoding virulence associated surface structures of pathogenic Gram-negative bacteria, such as *Escherichia coli, Haemophilus influenzae, Salmonella enteriditis, Salmonella typhimurium, Bordetella pertussis, Yersinia enterocolitica, Yersinia pestis, Helicobacter pyroli* and *Kebsiella pneumoniae* been identified as members of a particular family using the chaperone/usher protein assisted assembly pathway (Thanassi, D. G. et al., 1998, Curr. Opin. Microbiol. 1, pp. 223-231; Soto, G. E. and Hultgren, S. J.,1999, J. Bacteriol. 181, pp. 1059-1071).

In contrast to the apparent complexity of the general secretory (Type II; Karlyshev, A. V. and MacIntyre, S., 1995, Gene 158, pp. 77-82) and contact mediated (Type III; Lory, S., 1998, Curr. Opin. Microbiol. 1, pp. 27-35) pathways the chaperone/usher pathway appears to be rather simple and specific for secreting structural subunits. In addition to the structural subunits, these latter operons encode only two proteins involved in export and assembly. One is a periplasmic chaperone, which shows specificity for the structural subunit(s). The other one is a large outer membrane usher protein, which is required for translocation across the outer membrane, and which may form a large gated channel. The prototype of this pathway has been the PapD chaperone/PapC usher mediated assembly of Pap pili of *Escherichia coli* uropathogenic strain (Thanassi, D. G. et al., 1998, Curr. Opin. Microbiol. 1, pp. 223-231). The 3D-dimensional structure of PapD has been solved (Holmgren, A. and Branden, C. I., 1989, Nature 342, pp. 248-251). It has two domains, each with β-barrel and an immunoglobulin (Ig)-like fold.

Based on conserved differences in the primary structure of periplasmic chaperones and of organelle subunits, chaperone/usher systems may be divided into two subfamilies (denoted FGS and FGL) (Zav'yalov, V. P. et al., 1995, FEMS Immunol. Med. Microbiol. 11, pp. 19-24; Hung, D. L. et al., 1996, EMBO J. 15, pp. 3792-3805) involved in the assembly of morphologically distinct surface structures. FGS chaperone/usher systems are used for assembly of rod-like organelles (e.g. P and type 1 pili in *E. coli*), whereas thin aggregative fibrillar adhesins (TAFA) are assembled by FGL systems.

FGL chaperones are characterized by an extended variable sequence between the F1 and G1 β-strands, a disulfide bond connecting these two strands, and an extended N-terminal sequence (Zav'yalov, V. et al., 1997, Biochem. J. 324, pp. 571-578; Chapman, D. A et al., 1999, J Bacteriol. 181, pp. 2422-2429).

The crystal structures of the P pilus PapD-PapK chaperone-adapter subunit complex (Sauer, F. G. et al., 1999, Science 285, pp. 1058-1061) and the type 1 pilus FimC-FimH chaperone-adhesin complex (Choudhury, D. et al., 1999, Science 285, pp. 1061-1066) have revealed that pilin subunits, just as the chaperones, have Ig-like folds. However, the final (seventh) β-strand of the fold is missing, creating a deep cleft on the surface of the subunit where part of the hydrophobic core is exposed. The chaperone binds to the pilin domain by donating its G1 β-strand to complete the pilin Ig-like fold (Sauer, F. G. et al., 1999, Science 285, pp. 1058-1061; Choudhury, D. et al., 1999, Science 285, pp. 1061-1066). The chaperone G1 β-strand is inserted into the pilin acceptor cleft with extensive main-chain-to-main-chain hydrogen bonding between the donor strand and the two pilin edge strands (A and F) that define the perimeters of the acceptor cleft. Alternating hydrophobic side chains in the G1 strand bind in subpockets within the acceptor cleft and complete the hydrophobic core of the pilin domain. Assembly of subunits is thought to proceed by a donor strand exchange mechanism in which the chaperone G1 donor strand interaction is replaced by a similar interaction between subunits (Sauer, F. G. et al., 1999, Science 285, pp. 1058-1061; Choudhury, D. et al., 1999, Science 285, pp. 1061-1066). Indeed, the X-ray analysis of PapD-PapK complex showed that N-terminal sequence of the subunit composed of 10 residues is disordered in structure (Sauer, F. G. et al., 1999, Science 285, pp. 1058-1061). This sequence possesses highly conserved motif, which have been shown to participate in subunit-subunit interactions. This motif has homology to G1 β-strand of the chaperone (Soto, G. E. et al., 1998, EMBO J. 17, pp. 6155-6167). Because the N-terminal sequence apparently protrudes away from the main body of the chaperone-subunit complex, it would be free to exchange with G1 strand of the chaperone.

*Yersinia pestis* induced plague was one of the most devastating diseases of the last millennium. Over a third of the population of Europe is estimated to have died in the fourteenth century epidemic. Today, the World Health Organization reports 1,000 to 3,000 cases of plague every year. One of the *Y. pestis*-specific properties is the capability to form capsule. The ability to elaborate capsular material (fraction 1; F1) is associated with the resistance of bacteria to phagocytosis. Absence of only capsular F1 (Caf1) antigen synthesis in the infected strain leads to increased survival time of some animal host species (Drozdov, I. G. et al., 1995, J. Med. Microbiol. 42, pp. 264-268; Samoilova, S. V. et al., 1996, J. Med. Microbiol. 45, 440-444).

The nonpilus organelles (e.g. F1 capsular antigen and Dr adhesins) are composed of only one or sometimes two types of subunits. The F1 capsular antigen from the plaque pathogen *Yersinia pestis* consists of linear fibers of a single subunit (Caf1) and it serves as a prototype for nonpilus organelles assembled via the FGL chaperone/usher pathway. Therefore, while the F1 capsular antigen from *Yersinia* is used as the model in the present disclosure, the invention is related also to other microbes using the same assembly pathway. Urinary track infection (UTI) caused by *Eschericia coli* for example, is a severe health problem all over the world. Alone in the USA approximately 1 million patients are hospitalised each year due to this infectious disease.

Based on the particular properties of the primary structure of periplasmic chaperone, the caf operon, responsible for production and assembly of Caf1 antigen (Galyov, E. E. et al., 1990, FEBS Lett. 277, pp. 230-232), is related to FGL subfamily of chaperone/usher systems. It encodes a 26.5 kDa periplasmic chaperone Caf1M (Galyov, E. E. et al., 1991, FEBS Lett. 286, pp. 79-82) and a 90.4 kDa outer membrane usher protein Caf1A (Karlyshev, A. V. et al., 1992, FEBS Lett. 297, pp. 77-80) which together mediate surface assembly of Caf1 subunits in recombinant *E. coli* (Karlyshev, A. V. et al., 1994, NATO ASI Series, v. 11, H 82, Biological Membranes: Structure, Biogenesis and Dynamics, pp. 321-330).

Accordingly, preventing the formation of adhesive organelles is therefore a promising concept to prevent the bacteria to infect host tissues. There are disclosures showing various potential compounds to prevent the formation of adhesive organelles. However, basically these inventions disclose clearly more complex compounds than the present disclosure. Moreover, the prior art concentrates in the peptides of the G1 β-strand as being potential antimicrobials.

U.S. patent application 0030099665 discloses a vaccine against bacterial infections comprising a complex of a bacterial chaperone protein with an adhesin protein or an mannose binding immunogenic fragment of the adhesin protein. The vaccine is especially for treating of urinary tract infection.

U.S. patent application Ser. No. 20020086037 discloses a protein construct comprising a pilus protein portion an a donor strand complementary segment.

U.S. Pat. No. 6,001,823 discloses a method to screen for drugs against diseases caused by tissue-adhering bacteria. The method is based predicting the binding energy of a putative drug molecule to the chaperone.

In this invention surprisingly we found that only short peptide sequences (about 6 amino acid residues) at the N-terminal extension of Caf1 subunit are critical for Caf1 polymerization and expression on bacterial surfaces. Surprisingly, we additionally observed that peptides corresponding to the sequences effectively inhibited surface expression of Caf1.

SUMMARY OF THE INVENTION

The present invention provides antimicrobials for efficient therapy of infections caused by bacterial pathogens. The antimicrobials include peptides corresponding to the active site of N-terminal extension of subunits composing specific adhesive organelles of virulence of pathogenic bacteria. These antimicrobial peptides inhibit surface expression of adhesive organelles and thus prevent development of infections caused by pathogenic bacteria. This invention further provides a novel screening method to obtain molecules with antimicrobial characteristics.

BRIEF DESCRIPTION OF DRAWINGS

FIG. 6. Determination of the active site in the N-terminal extension of Caf1. The amino acid residues are shown by one letter code. The number of residue corresponds to its position in mature Caf1 (Galyov, E. E. et al., 1990, FEBS Lett. 277, pp. 230-232). The positions of deleted residues are shown by asterisks. The positions of changed residues are shown by italic.

Figure 8:
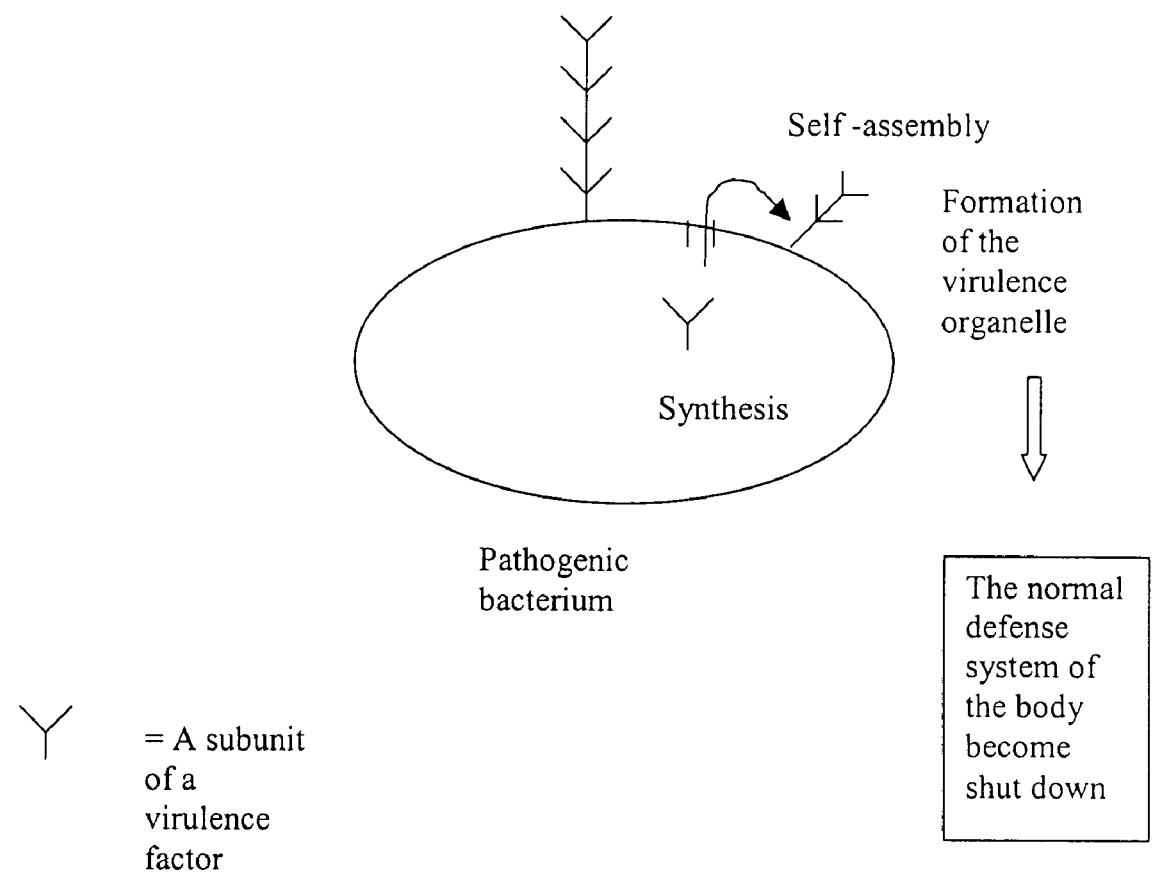

FIG. 8. Prior Art. Formation of pathogenic features of a microbe.

FIG. 9. Prevention of formation of pathogenic features of a microbe according to the present disclosure.

A. A non effective drug molecule does not prevent polymerization of the subunits of the virulence factor.

B. An effective drug molecule prevents polymerization of the subunits of the virulence factor.

FIG. 11. Table 1. Alignement of N-terminal Amino Acid Sequneces of GL Subunits with Caf1$G_d$ donor strand.

DETAILED DESCRIPTION OF THE INVENTION

The present invention relates to prevention of pathogenic event of Gram negative bacteria and to treating bacterial infections.

During the pilus assembly via the donor-strand mechanism the N-terminal extension of a subunit is complemented by G1 β-strand of a corresponding chaperone. On the contrary to the prior art suggesting that the G1 β-strand peptides to be useful as potential antimicrobials we show that the peptides corresponding to the amino-terminal extension subunits are a novel source of antimicrobial peptides.

In this invention, there were surprisingly observed that (i) interactions between subunits are stronger than chaperone-subunit interactions; (ii) only a short part of the amino-terminal extension of subunits is critical for their polymerization and surface expression. Accordingly the present invention relates to peptides corresponding to the amino-terminal extension of subunits being more potential antimicrobials than peptides from the G1 β-strand of chaperones. Another aspect of the present invention is that not all the sequence of the amino-terminal extention of subunit but a short peptide corresponding to the active site can be used as antimicrobial.

The present invention is further illustrated by the following, non-limiting examples. Whereas the examples deal with peptides of certain sequences, it is evident that any compounds mimicking the peptide conformations and binding to the site, critical for the polymerization, can be used as the drugs preventing formation of adhesive organelles.

EXAMPLE 1

Evidence that linear Caf1M-(Caf1)$_n$ complexes accumulate in the periplasm in the absence of Caf1A usher Plasmids pFM1, pFM'1S and pTCA1 are described in details in Chapman, D. A., Zavialov, A. V. Chernovskaya, T. V., Karlyshev, A., Zav'yalova, G. A., Vasiliev, A. M., Dudich, I. V., Abramov, V. M., Zay'yalov, V. P., and MacIntyre, S. (1999). Structural and functional significance of the FGL sequence of the perimlasmic chaperone Caf1M of *Yersinia pestis*. J. Bacteriol. 181, 2422-2429.

Figure 1:
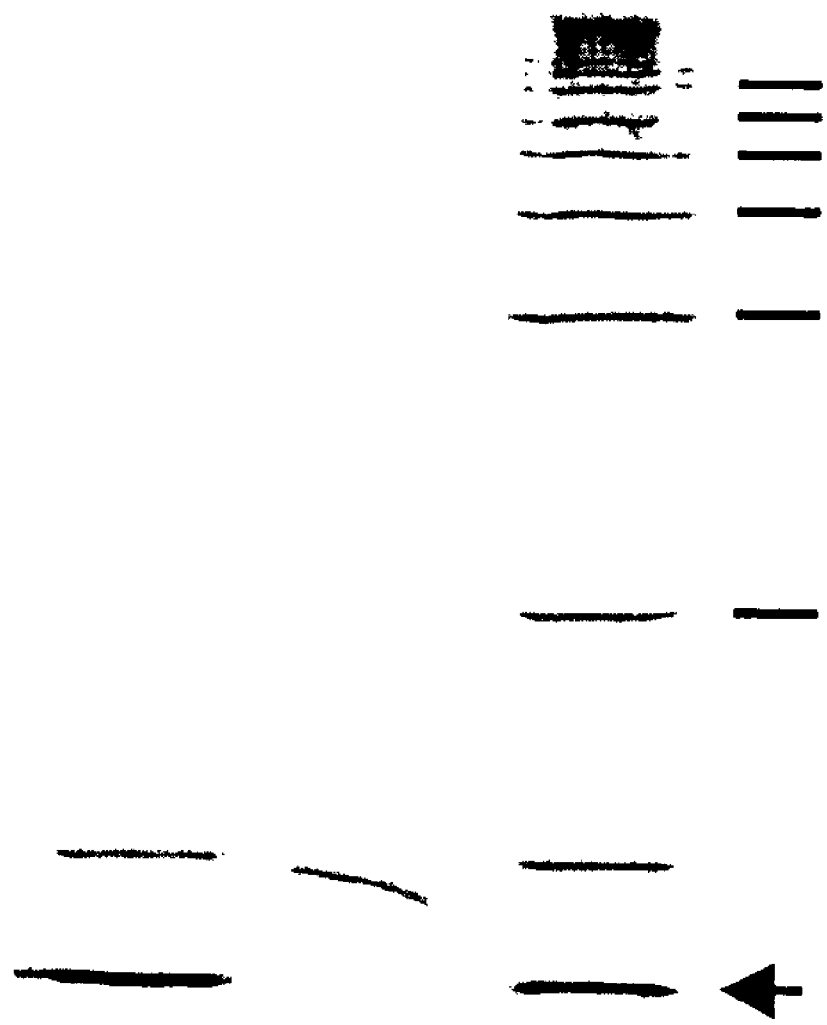
FIG. 1. Accumulation of heterogeneous Caf1M-Caf1 complexes in the periplasm in the absence of Caf1A. Isoelectric focusing (4.5-6 pH gradient) coomassie blue-stained gel of periplasmic extracts of *E. coli* DH5α cells carrying plasmids pFM1 (lane 1), pFM'1S (lane 2), and pTCA1 (lane 3). Bars show six well-resolved Caf1M-Caf1$_n$ complexes [Caf1M and Caf1 detected with anti-Caf1M and anti-Caf1 antibody by immunoblotting similar gel (not shown)], arrow shows position of free Caf1M.
Figure 2:
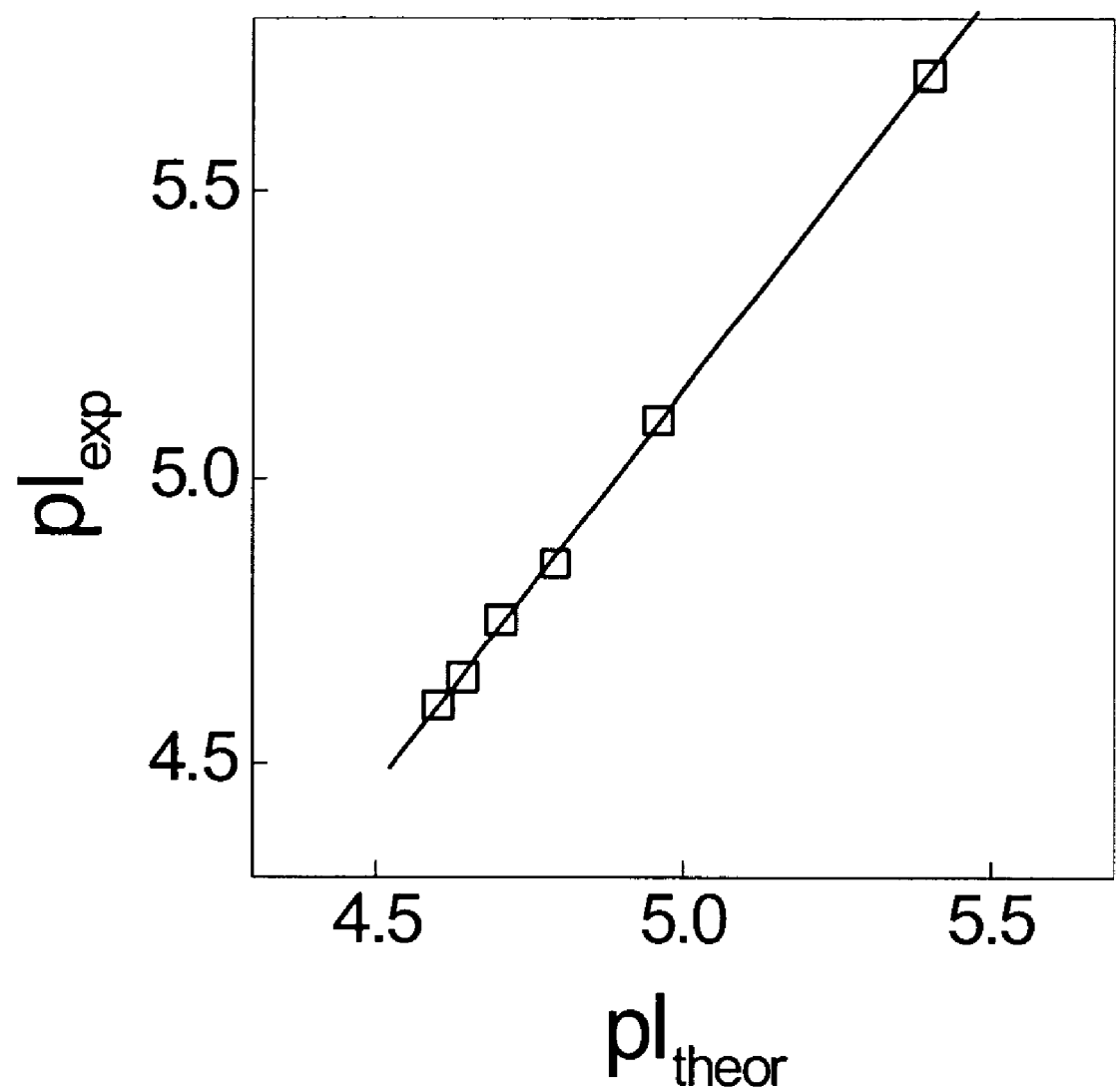
FIG. 2. Comparison of experimentally and theoretically found pI of Caf1M monomer, Caf1 polymer, and Caf1M-(Caf1)$_n$ complexes. Experimental data were obtained with isoelectrofocusing (IEF) using precast 3-9 and 4-6.5 pI gradient gels and IEF calibration kit (Pharmacia, Sweden). The theoretical data were calculated on the basis of protein sequences using the DNASTAR Protean program (DNASTAR Inc., USA). For theoretical estimation of pI of the complexes the fusion sequences of Caf1M and (Caf1)$_n$ were used.

Isoelectric focusing (IEF) of periplasmic extract of DH5α/pFM1 cells expressing Caf1M and Caf1, revealed a ladder of bands starting from pI 5.7 and approaching pI 4.4 (FIG. 1, lane 1) that was not observed on gels of periplasmic extract of DH5α/pFM'1S cells expressing Caf1 alone (FIG. 1, lane 2) or DH5α/pTCA1 cells expressing Caf1M alone (FIG. 1, lane 3). Similarly, a ladder of bands was observed on native gradient gels of DH5α/pFM1 but not DH5α/pFM'1S or DH5α/pTCA1 periplasmic extract (FIG. 1*b*). Since Caf1 subunits polymerize to form F1 antigen, whereas the Caf1M chaperone equilibrates between monomer and dimer forms in solution, it is reasonable to argue that the bands in the ladder might represent different Caf1 polymers, possibly capped by a single copy of Caf1M chaperone. The presence of Caf1M chaperone and Caf1 subunit in each band was confirmed using polyclonal anti-Caf1M and and-F1 antigen. The pIs of the six best resolved bands correlated well with the theoretically calculated pIs of Caf1M-Caf1 chaperone-subunit complexes composed of a single copy of Caf1M chaperone and 1-6 copies of Caf1 subunit (FIG. 2).

Figure 3:
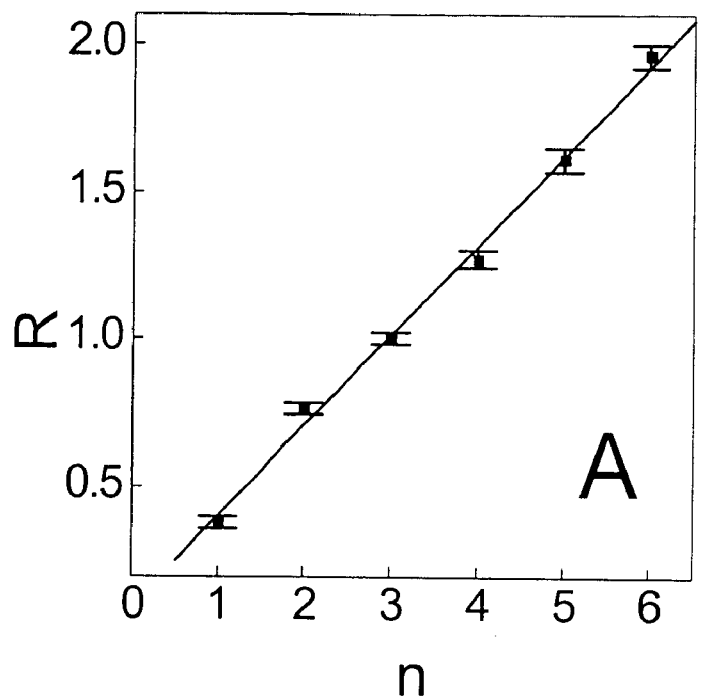
FIG. 3. Caf1M-(Caf1)$_n$ periplasmic chaperone-subunit complexes have rod- or coil-like structures. (A) Ratio of coomassie blue R-250 binding of Caf1 and Caf1M in the first six low-MW complexes as a function of assumed stoichiometry coefficient n. The line was drawn with a slope of 0.31±0.01 representing the ratio of coomassie blue binding by Caf1 and Caf1 of Caf1-Caf1M complex. The data were obtained from quantitative scanning of the bands of Caf1 and Caf1M in coomassie blue R-250 stained SDS PAGE gels of purified complexes. Each point represents the mean of data obtained from loading 2, 4 and 8 μg of purified complex, bars represent 2σ. (B) Gel filtration of the purified complexes. A Superose 12 10/30 column was calibrated with the globular proteins (squares) chymotrypsinogen, ovalbumin, bovine serum albumin, aldolase, and ferritin. The void volume was determined with blue dextran. Circles represent the $K_{av}$ of the complexes as a function of calculated MW. The lines drawn for the data for globular proteins and complexes starting with n=2 have slopes 0.210±0.035 and 0.411±0.009, correspondingly.
Figure 3:
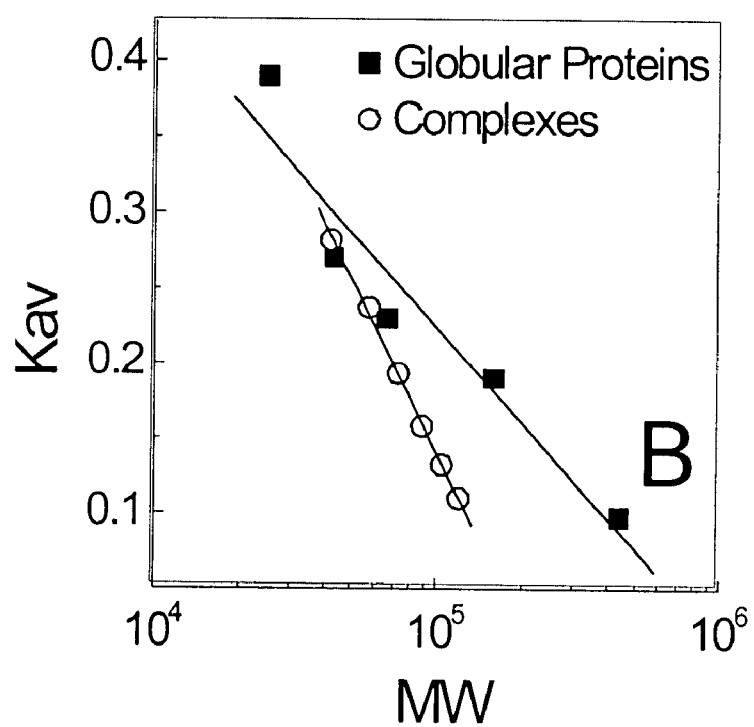

For further characterization, six complexes were purified. The Caf1M-(Caf1)$_2$ complex was 95% pure, while the rest of the complexes contained 85-95% of pure protein as judged by SDS PAGE. The stoichiometry of the purified complexes was determined by quantification of coomassie blue binding to Caf1M and Caf1 after SDS PAGE of complexes. Ratios (R) of coomassie blue binding by Caf1M and Caf1 obtained for each purified complex were plotted against the ordinal number (n) of complexes in their distribution by pI from basic to acidic (FIG. 3A). The function appeared to be linear with a slope γ of 0.31±0.01. This value fits reasonably well with the expected value estimated from the relative content of coomassie blue binding residues (Comton, S. J. and Jones, C. G., 1985, Anal. Biochem. 151, 369-374) in Caf1 compared to Caf1M ($R_{basic+aromatic}$=0.4, $R_{Arg}$=0.33, and $R_{basic+Trp}$=0.32). The other complexes had R-values approximately equal to 0.31n, showing that each next complex with lower pI contains one additional Caf1 subunit.

To further analyze the different Caf1M-(Caf1)$_n$ complexes they were subjected to analytical gel chromatography (FIG. 3B). The $K_{av}$ values for the complexes were plotted against the log of the assumed MW (FIG. 3B, circles). Starting from the second complex, the dependence was linear suggesting that the MWs had been correctly estimated. However, the line obtained from the complexes, and the linear calibration obtained from standard globular proteins (FIG. 3B, squares) had different slopes. The ratio of the slopes for complexes (K=0.411±0.009) and globular proteins (k=0.21±0.035) was about 2. This shows that the complexes have a larger hydrodynamic radius of gyration than expected for globular proteins of similar size, indicating that Caf1M-Caf1$_n$ complexes with two or more Caf1 subunits have coil-like or flexible rod-like shapes (Yau, W. W. and Bly, D. D., 1980, in: Size Exclusion Chromatography, Provder, T., ed., ACS Symposium Series, American Chemical Society, Washington, D.C., pp. 197-204). The $K_{av}$ of the smallest complex (Caf1M-Caf1; estimated MW 44.3 kDa) did not fit well to the line obtained for higher-order complexes, but did fit to the linear calibration for globular proteins, where its MW is determined as 40-60 kDa and its $K_{av}$ was almost the same as that of ovalbumin (43 kDa). Assuming a similar mode of binding as observed for the PapD-PapK and FimC-FimH chaperone-subunit complexes (Sauer, F. G. et al., 1999, Science 285, pp. 1058-1061; Choudhury, D. et al., 1999, Science 285, pp. 1061-1066), the shape of the Caf1M-Caf1 complex is expected to be roughly spherical.

Figure 4:
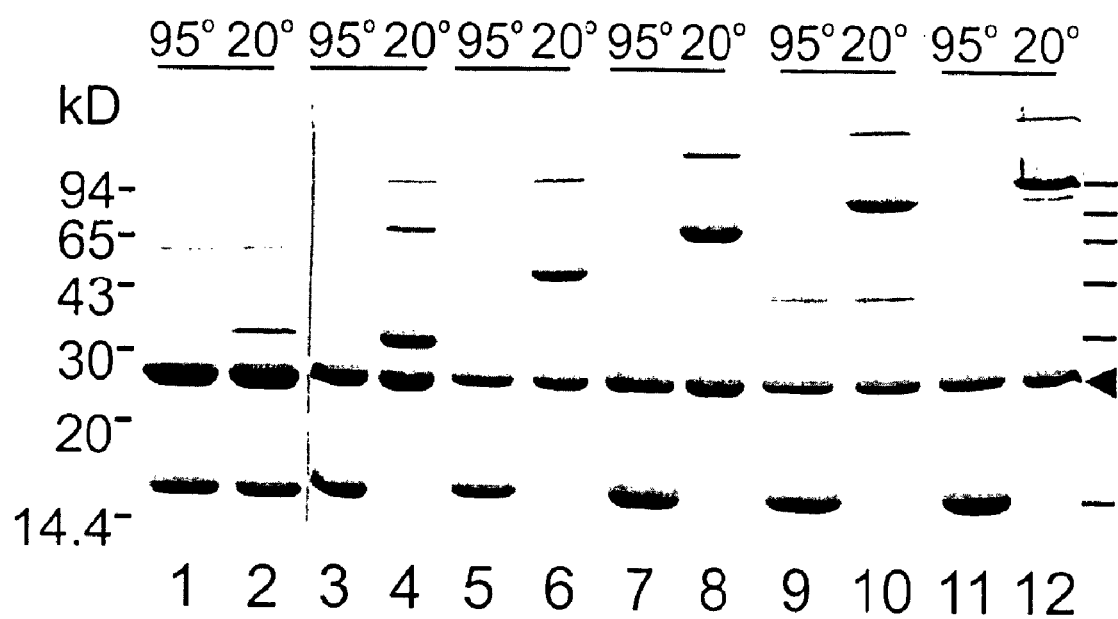
FIG. 4. Interactions between subunits in Caf1M-(Caf1)$_n$ complexes are more resistant to SDS than interactions between chaperone and subunit. SDS PAGE of periplasmic extract of DH5α/pFM1 cells (lanes 1, 2), and purified complexes Caf1M-(Caf1)$_n$: n=2 (lanes 3, 4), n=3 (lanes 5, 6), n=4 (lanes 7, 8), n=5 (lanes 9, 10), n=6 (lanes 11, 12), pre-incubated with 0.1% SDS at 20° C., and at 95° C.

Evidence that subunit interactions are stronger than chaperone-subunit interactions To gain more insight into the structure of the complexes the stability of Caf1M-Caf1 and Caf1-Caf1 interactions in higher-MW complexes towards 0.1% SDS treatment at 20° C. and at 95° C. was compared (FIG. 4). After SDS treatment, the samples were subjected to PAGE and stained with coomassie blue. Regardless of temperature, in all cases Caf1M dissociated from the complexes and moved as a single band. In contrast, dissociation of Caf1 subunit required treatment at 95° C., which resulted in more or less all of the subunit being detected as monomer.

Evidence that Caf1 polymerization requires an N-terminal donor strand

Figure 5:
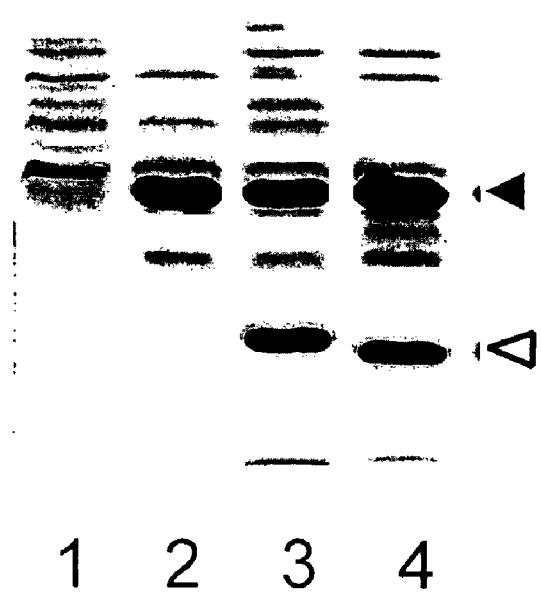
FIG. 5. Deletion of a six amino acid sequence at the N-terminus of Caf1 abolishes polymerization. (A) Comparison of N-terminal sequences of wt Caf1 and mutant ΔCaf1. The deleted sequence is underlined. The introduced Ser at position 9 of ΔCaf1 is shown in italic. Hydrophobic amino acid residues are shown in bold. (B) Coomassie blue-stained SDS PAGE gel of *E. coli* DH5α cells carrying plasmids pTrc99a (lane 1), pTCA (lane 2), pFM1 (lane 3), and pΔFM1 (lane 4). Open arrow head shows positions of Caf1 and ΔCaf1 (moves slightly faster), black arrow head shows position of Caf1M. (C) IEF (4.5-6 pH gradient) coomassie blue-stained gel of the same samples as in (B). Arrow shows the position of the Caf1M-ΔCaf1 complex.
Figure 5:
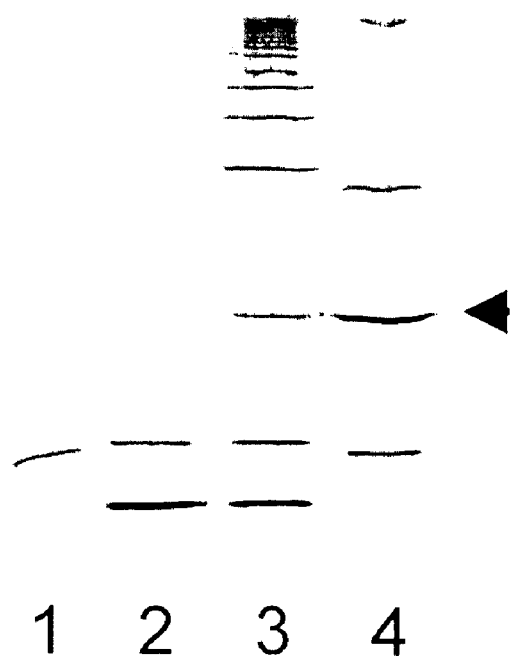

Conserved motif at the N-terminus of structural subunits of pili has been shown to be important for subunit-subunit interactions (Soto, G. E. et al., 1998, EMBO J. 17, 6155-6167). It was proposed, that in pilus, every subunit donates this motif to neighboring subunit, complementing its Ig-like fold (Sauer, F. G. et al., 1999, Science 285, pp. 1058-1061; Choudhury, D. et al., 1999, Science 285, pp. 1061-1066). To elucidate the existence of the donor strand complementation between Caf1 subunits in F1-capsule, a mutant of Caf1 with a deleted sequence close to its N-terminus was constructed (ΔCaf1). The deleted sequence of 6 amino acids contained 4 hydrophobic residues alternating with threonines (FIG. 5A) showed a high potential to form a hydrophobic β-strand. The construction procedure required leaving an additional amino acid at the place of the deletion. Therefore, a Ser residue at position 9 was inserted (FIG. 5A). A Ser-Thr-Thr-Ser peptide composed of similar amino acids appeared close to N-terminus of Caf1. This peptide with predicted disordered structure is unable to form β-strands and may strengthen disturbing effect of the deletion. The gene encoding wt Caf1 located on the designed earlier plasmids pFM1 (Caf1, Caf1M) and pFMA1 (Caf1, Caf1M, and Caf1A) was replaced with that of deletion mutant to obtain pdFM1 and pdFMA1, which were used further in co-expression experiments.

SDS PAGE of periplasmic extracts of *E. coli* DH5α cells, harboring plasmid pΔFM1, (FIG. 5B, lane 4) revealed two intensive bands that were absent in control extracts of *E. coli* DH5α/pTrc99a (FIG. 5B, lane 1). One of these bands, moving with MW of 27 kDa, was identical to the band of Caf1M seen in SDS PAGE of the periplasmic extract of *E. coli* DH5α cells transformed with pTCA (lane 2). The other band, moving slightly faster than the band of Caf1 in SDS PAGE of periplasmic extract of *E. coli* DH5α/pFM1cells (lane 3, a strong band under the band of Caf1M), without doubts, corresponded to ΔCaf1. The bands of Caf1 and ΔCaf1 had almost similar intensities, indicating that chaperone extracts ΔCaf1 from inner membrane and protects it from proteolysis as successfully as it does with wt subunit. However, IEF of the periplasmic extracts of *E. coli* DH5α cells harboring plasmid pΔFM1 (FIG. 5C, lane 4) did not reveal the characteristic ladder of chaperone-subunit complexes that was observed in periplasmic extracts of cells co-expressing wt Caf1 with Caf1M (lane 3). Instead, there was only one band additional to the control bands of high intensity, having pI similar to that of Caf1M-Caf1 complex. This shows that introduced deletion abolished polymerization of ΔCaf1 in the periplasm, resulting accumulation of high levels of binary Caf1M-ΔCaf1 complex.

Ability of ΔCaf1 to assemble on the surface of cells was investigated by examining of intact *E. coli* DH5α cells, harboring pdFMA, with polyclonal anti-Caf1 antibody. The antibody binding was evaluated by counting fluorescence after following treatment of cells with FITC-labeled secondary antibody. These cells showed similar fluorescence (37.2±5.5 cps) to that of negative controls (*E. coli* DH5α cells/pTrc99a, 32.6±4.0 cps), while *E. coli* DH5α cells harboring pFMA revealed about 200-times more intensive fluorescence (7200±226 cps). Thus, ΔCaf1 clearly was not assembled on the cell surface and the N-terminal extension therefore is essential for the subunit polymerization.

Determination of the active part of N-terminal extention

For determination of the active part of N-terminal extension the different mutant forms of Caf1 were produced (FIG. 6). It can be seen from the obtained data that only middle part of the N-terminal extension of about 6 amino acid residues is critical for polymerization of Caf1.

EXAMPLE 2

The peptide Ala-Thr-Ala-Thr-Leu-Val corresponding to the active site of Caf1 N-terminal extension was synthesized by solid phase synthesis. *E. coli* DH5α cells harbouring plasmid pFMA were grown to $A_{600\,nm}=0.6$ in LB medium (Maniatis, T. et al., 1989, in: Molecular Cloning: A Laboratory Manuel, 2nd edn., Cold Spring Harbor Laboratory Press, Cold Spring Harbor) containing 70 mg/l of ampicillin and the peptide in the range of concentrations from $10^{-4}$ to $10^{-8}$ M. As the control *E. coli* DH5α cells harbouring plasmid pFMA were grown to the same concentration of cells in LB medium without the peptide. Protein expression was induced with 0.5 mM IPTG during 1.5 h. The expression of Caf1 on the surface of cells was investigated with polyclonal anti-Caf1 antibody. The antibody binding was evaluated by counting fluorescence after following treatment of cells with FITC-labeled secondary antibody. The cells grown in the LB medium containing the peptide in the range of concentrations from $10^{-4}$ to $10^{-8}$ M showed similar fluorescence (from 30±5.0 to 40±5.5 cps) to that of negative controls (*E. coli* DH5α cells/pTrc99a, 32.6±4.0 cps), while the cells grown in the absence of the peptide revealed about 200-times more intensive fluorescence (7200±226 cps). Thus, the peptide Ala-Thr-Ala-Thr-Leu-Val in the range of concentrations from $10^{-4}$ to $10^{-8}$ M clearly inhibits the expression of Caf1 on the surface of cells.

EXAMPLE 3

Assembling of Caf1 in an usher-free in vitro system.

Figure 7:
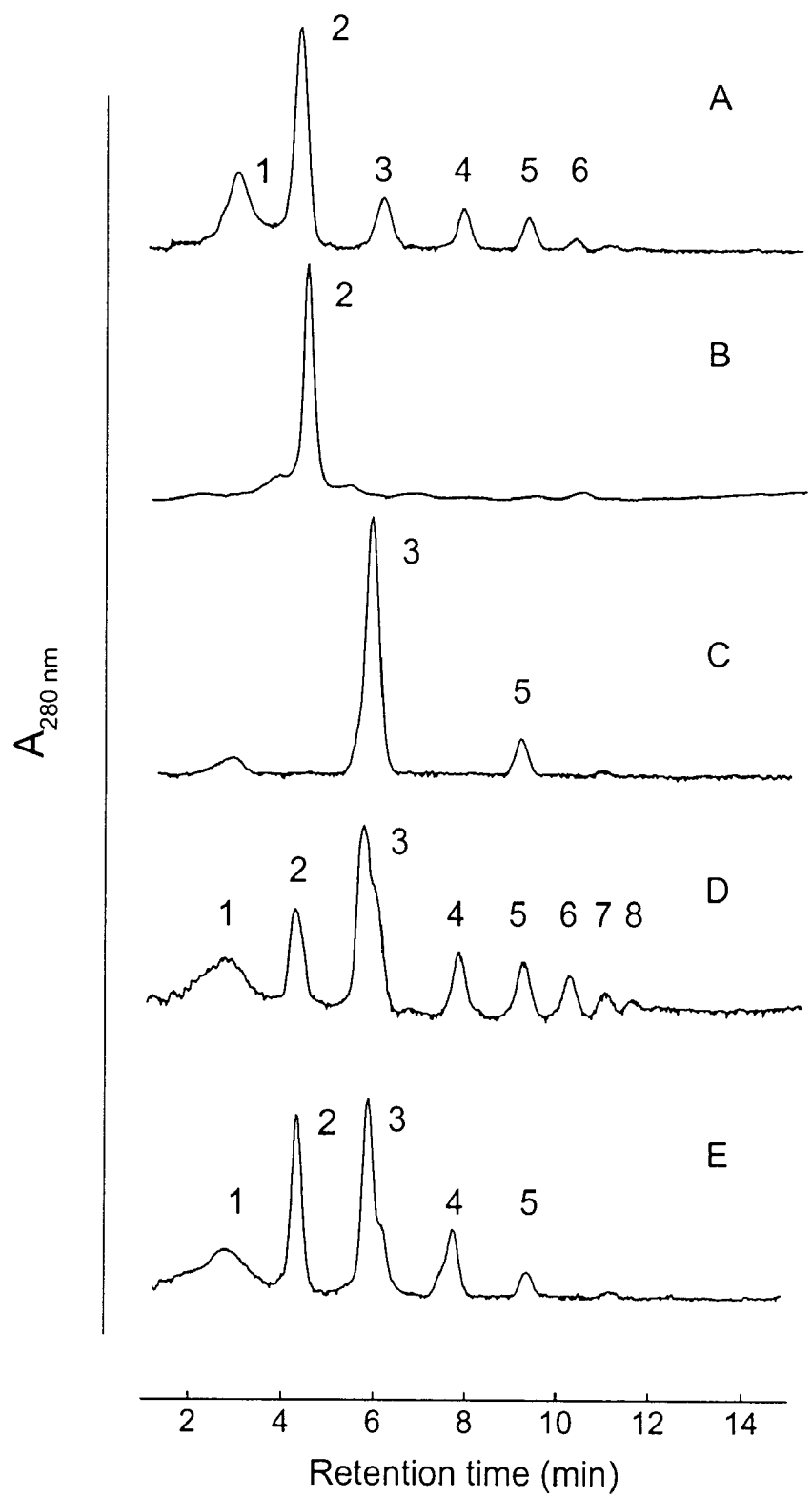
FIG. 7. Polymerization of Caf1 in vitro. Freshly purified complexes CafM-Caf1 (A), Caf1M-ΔCaf1 (B), Caf1M-(Caf1)2 (C), and approximately equimolar mixtures of Caf1M-(Caf1)2 with CafM-Caf1 (D), and Caf1M-(Caf1)2 with Caf1M-ΔCaf1 (E) were incubated for 2 h at 25° C. The samples were diluted in 20 mM Tris-HCl, pH 7.7 and fractionated on a Mono Q HR 5/5 anion exchange column with 0-300 mM NaCl gradient as the mobile phase. Characterized peaks of the elution curves are numbered: 1, Caf1M; 2, CafM-Caf1 or Caf1M-ΔCaf1; 3, Caf1M-(Caf1)2; 4, Caf1M-(Caf1)3 or Caf1M-(Caf1)2-ΔCaf1; 5, Caf1M-(Caf1)4; 6, Caf1M-(Caf1)5; 7, Caf1M-(Caf1)6; 8, Caf1M-(Caf1)7.
Figure 10:
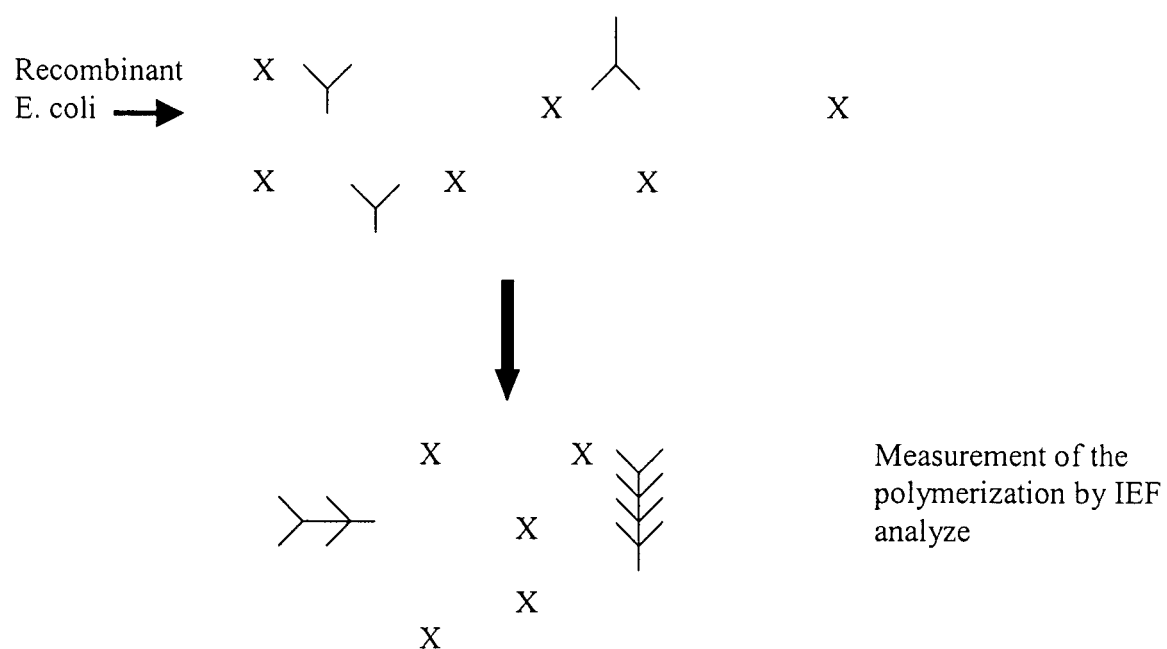
FIG. 10. The principle of the method to screen for potential molecules to prevent formation of pathogenic features.
Figure 10:
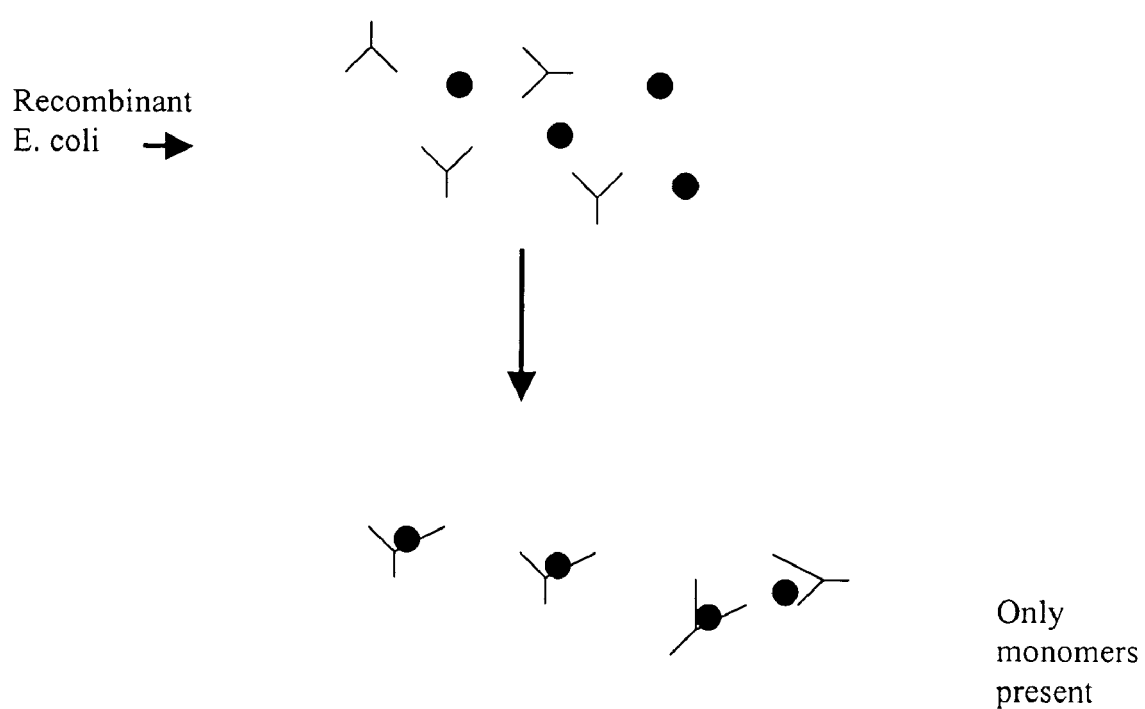

Fractionation of a sample of Caf1M-Caf1 pre-incubated during 2 h at 25° C. on a Mono Q HR column (Pharmacia, Sweden) in Tris-HCl, pH 7.7 with a linear 20-200 mM NaCl gradient revealed several peaks (FIG. 7A). IEF of the central fractions of the peaks 1-6 showed that they contain free Caf1M, and complexes Caf1M-(Caf1)$_n$ with n=1-5, correspondingly. Fractions contained peak 2 were pooled, Caf1M-Caf1 was quickly concentrated and incubated for 2 h at 25° C. Re-chromatography of this sample gave similar to the shown in FIG. 7A elution profile. Thus, incubation of the binary complex at room temperature led to formation of free Caf1M and higher-order complexes.

Pre-incubation of freshly purified Caf1M-(Caf1)$_2$ in the same conditions led to formation of small amount of Caf1M-(Caf1)$_4$ as fractionation of this sample shows in FIG. 7C, peak 5. Similarly, other purified complexes Caf1M-(Caf1)$_n$ gave small peaks, corresponding to Caf1M-(Caf1)$_{2n}$ and, at longer incubation times, also peaks, corresponding to Caf1M-(Caf1)$_{3n}$ (not shown). These additional complexes were also observed earlier in IEF gels of the concentrated preparations of Caf1M-(Caf1)$_n$, with n=2-6 (FIG. 2, faint band with lower pIs). However, fractionation of sample of approximately equimolar mixture of Caf1M-(Caf1)$_2$ with Caf1M-Caf1 pre-incubated in the same conditions revealed eight peaks, containing free Caf1M and Caf1M-(Caf1)$_n$ with n=1-7, correspondingly (FIG. 7D). The amounts of the newly formed higher-order complexes were notably lager than in preparations of the binary or ternary complexes incubated in the same conditions (compare elution curves on FIG. 7A, 7C and 7D). Similar enhanced reactivity was observed for mixtures of Caf1M-Caf1 with Caf1M-(Caf1)$_3$. However, incubation of mixtures of Caf1M-(Caf1)$_2$ with Caf1M-(Caf1)$_3$ did not lead to significant formation of higher-order complexes. This shows especial role of the binary complex in the inter-complex reactions. This method of study of polymerization of subunits in vitro can be used for selection of antimicrobials inhibiting both polymerization and surface expression of adhesive organelles of virulence of bacterial pathogens. As it was mentioned above ΔCaf1 can be considered as the example of antimicrobial inhibiting polymerization of subunits composing adhesive organelles of virulence. Indeed, on the contrary to the wt binary complex, purified Caf1M-ΔCaf1 did not form any higher-order complexes after long incubations (FIG. 7B).

Mixing of Caf1M-ΔCaf1 with Caf1M-(Caf1)$_2$ led to formation of a complex, eluting with the same volume as Caf1M-(Caf1)$_3$ and smaller amount of presumable Caf1M-(Caf1)$_4$, which normally accumulates in samples of Caf1M-(Caf1)$_2$ (FIG. 7C). In comparison to mixtures of wt binary and ternary complexes, this mixture did not contain significant amounts of other higher-order complexes (compare FIG. 7D and FIG. 7E). The new complex (peak 4) was purified, concentrated and mixed with Caf1M-ΔCaf1. No additional complexes were observed in this mixture. These results suggests that a single ΔCaf1 subunit can be incorporated at the uncapped end of Caf1M-(Caf1)$_2$ resulting in a Caf1M-(Caf1)$_2$-ΔCaf1 complex, which similarly to Caf1M-ΔCaf1 is inert to self-react or react with Caf1M-ΔCaf1. However, like Caf1M-ΔCaf1 it was able to react with wt complexes, for example with Caf1M-Caf1, supporting assumed distal from chaperone position of ΔCaf1 in Caf1M-(Caf1)$_2$-ΔCaf1 and suggesting that polymerization can occur from both sides of Caf1 polymer.

EXAMPLE 4

The in vitro system of Caf1 polymerization can be used for developing of a new method of selection of potential antimicrobials inhibiting polymerization of subunits composing adhesive organelles of virulence of bacterial pathogens. FIG. 9 is a schematic illustration of the principle of the screening method according to the present disclosure.

To study a potential of in vitro system for this aim the purified complex Caf1M-Caf1 was mixed with Caf1M-(Caf1)$_2$ and Caf1M-(Caf1)$_3$ (in same conditions as in Example 3) in the presence of the peptide Ala-Thr-Ala-Thr-Leu-Val (SEQ ID NO: 1) corresponding to the active site of Caf1 N-terminal extension in concentration from $10^{-4}$ to $10^{-10}$ M. No high molecular weight complexes were observed after long incubations at concentrations from $10^{-4}$ to $10^{-6}$. Moreover, some dissociation of the complexes to free Caf1M and Caf1 was evident. Thus, polymerization was completely inhibited in the range of concentrations close to equimolar mixtures of the complexes and the peptide.

EXAMPLE 5

Alignment of N-terminal amino acid sequences of FGL subunits is shown in FIG. 11. Residues corresponding to donor strand residues of Caf1 are shaded. Two positions (dark shaded) appear most restricted. The last donor residue most frequently has large hydrophobic side chain (leucine or isoleucine), and residue two donor positions upstream of this is always a small residue (alanine or glycine). The analysis reveals potential polymerisation-inhibitor sequences, which should include region between two most restricted positions and optionally 2-3 amino acids beyond this region.

A pDrhe562 expression plasmid carrying full operone for Dr hemagglutinin assembly was constructed based on a pTrc99a plasmid (Pharmacia, Sweden). Dr hemagglutinin, chaperone, and usher genes were amplified by PCR using isolate of total chromosome obtained from a XS5001 *E. coli* strain (JBL, University of Turku). The DH5a cells transformed with pDrhem562 agglutinate human reticulocytes, indicating assembly of Dr hemagglutinin of the cell surface. Adding of a TTGTTKL peptide (SEQ ID NO:2) (synthesized by solid phase synthesis) at mM concentration to DH5a cells/pDrhem562 cells growing in all growth phases completely abolished polymerisation of Dr hemagglutinin, as judged by hemaglutination assay at cell density up to one milliard cell/ml. This example shows that suggested sequences most likely can inhibit assembly of all corresponding capsular adhesins. Other putative sequences are GTTGTTKL (SEQ ID NO:3) and TTKL (SEQ ID NO:4).

Inhibition of Dr adhesin assembly is extremely important for public health care, since it plays a role in the initiation of the urinary tract (UT) infections (P and type I pili in *E. coli*). Only in USA 1 billion USD is spent annually for treatment of UT infections and they are on the second place after oral infections by amount of cases Based on experimental and computer modeling results, the universal inhibitor is evidently TXTYTZ (SEQ ID NO:5), where T is Thr, X is either Ala or Gly, Y is either Ala, Thr or Val, Z is either Ile or Val.

What is claimed is:

1. An antimicrobial peptide consisting of the sequence Thr-Ala-Thr-Val-Thr-Val-(SEQ ID NO: 1), wherein the antimicrobial peptide is capable of inhibiting formation of surface adhesive organelles of pathogenic Gram negative bacteria by inhibiting self polymerization of equal peptides units; is capable of binding with a binding constant of $10(3)$ M or higher with a polymerizing protein unit; and is effective in inhibiting self-polymerization of bacterial virulence organelles in a concentration less than $10(-4)$ M.

2. A method to treat bacterial infections by inhibiting self-polymerization of equal peptide units of bacterial surface adhesive organelles, thereby inhibiting formation of said surface adhesive organelles, said method further comprising administering to a patient a therapeutically active amount of the antimicrobial peptide of claim 1.

3. The method according to claim 2 wherein the antimicrobial peptide is further bound to a small molecular or macromolecular substance, thereby increasing the stability of the peptide.

4. The method according to claim 2 wherein the antimicrobial peptide is applied orally, subcutaneously, or injected into blood circulation.

5. The method according to claim 4 wherein the antimicrobial peptide is applied in a concentration between $10^{-4}$ M to $10^{-10}$ M in sera during or treatment of microbial infections.

* * * * *

SEQUENCE LISTING

<160> NUMBER OF SEQ ID NOS: 5

<210> SEQ ID NO 1
<211> LENGTH: 6
<212> TYPE: PRT
<213> ORGANISM: artificial
<220> FEATURE:
<223> OTHER INFORMATION: coresponds to the active site of Caf1
      N-terminal extension

<400> SEQUENCE: 1

Ala Thr Ala Thr Leu Val
1               5

<210> SEQ ID NO 2
<211> LENGTH: 7
<212> TYPE: PRT
<213> ORGANISM: artificial
<220> FEATURE:
<223> OTHER INFORMATION: Synthesized

```
<400> SEQUENCE: 2

Thr Thr Gly Thr Thr Lys Leu
1               5

<210> SEQ ID NO 3
<211> LENGTH: 8
<212> TYPE: PRT
<213> ORGANISM: artificial
<220> FEATURE:
<223> OTHER INFORMATION: Synthesized

<400> SEQUENCE: 3

Gly Thr Thr Gly Thr Thr Lys Leu
1               5

<210> SEQ ID NO 4
<211> LENGTH: 4
<212> TYPE: PRT
<213> ORGANISM: artificial
<220> FEATURE:
<223> OTHER INFORMATION: synthesized

<400> SEQUENCE: 4

Thr Thr Lys Leu
1

<210> SEQ ID NO 5
<211> LENGTH: 6
<212> TYPE: PRT
<213> ORGANISM: artificial
<220> FEATURE:
<223> OTHER INFORMATION: synthesized
<220> FEATURE:
<221> NAME/KEY: misc_feature
<222> LOCATION: (2)..(2)
<223> OTHER INFORMATION: Xaa is either Ala or gly
<220> FEATURE:
<221> NAME/KEY: misc_feature
<222> LOCATION: (4)..(4)
<223> OTHER INFORMATION: Xaa is either Ala, Thr or Val
<220> FEATURE:
<221> NAME/KEY: misc_feature
<222> LOCATION: (6)..(6)
<223> OTHER INFORMATION: Xaa is either Ile or Val

<400> SEQUENCE: 5

Thr Xaa Thr Xaa Thr Xaa
1               5
```